US006261771B1

(12) United States Patent
Bohannon

(10) Patent No.: US 6,261,771 B1
(45) Date of Patent: Jul. 17, 2001

(54) METHOD AND APPARATUS FOR DETECTION OF MULTIPLE NUCLEIC ACID SEQUENCES AND MULTIPLE ANTIGENS

(75) Inventor: Robert C. Bohannon, Sherwood, OR (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 0 days.

(21) Appl. No.: 09/187,718

(22) Filed: Nov. 9, 1998

Related U.S. Application Data

(63) Continuation-in-part of application No. 09/025,470, filed on Feb. 18, 1998.

(51) Int. Cl.[7] ............................................. C12Q 1/68
(52) U.S. Cl. .................. 435/6; 435/91.1; 435/91.2; 435/91.5; 435/283.1; 435/286.5; 435/289.1; 435/293.1; 435/303.1; 436/501; 935/85; 935/88; 422/68.1; 422/80; 422/62; 422/82.05; 422/99; 422/129; 422/131; 422/132; 422/138; 422/149; 422/188; 422/198
(58) Field of Search ..................... 435/6, 91.1, 91.2, 435/91.5, 283.1, 286.5, 289.1, 293.1, 303.1; 422/68.1, 50, 62, 82.05, 99, 129, 131, 132, 134, 138, 148, 188, 198, 202, 203; 436/501; 935/85, 88

(56) References Cited

U.S. PATENT DOCUMENTS 5,779,977 * 7/1998 Haff et al. ........................ 422/68.1

\* cited by examiner

*Primary Examiner*—W. Gary Jones
*Assistant Examiner*—Janell E. Taylor
(74) *Attorney, Agent, or Firm*—William Randolph; William Medsger; Edward Stolarun

(57) ABSTRACT

A method and apparatus for detection of multiple target nucleic acids and/or antigens such as hormones, antibodies, or nerve agents in a sample, involves presenting the sample to a plurality of reporter binding sites wherein each reporter binding site comprises two partially hybridized molecules. A first of the two hybridized molecules is bound to the binding site and is complementary to a target nucleic acid or antigen, and it will therefore hybridize to the target nucleic acid or antigen and cause the release of the second hybridized molecule into the sample. The second hybridized molecule comprises a reporter nucleic acid sequence, which uniquely identifies the target nucleic acid or antigen. Subsequent PCR amplification of the unique reporter nucleic acid sequence using labeled primers results in multiple labeled copies of the unique nucleic acid sequence. The sample with the amplified and labeled copies of the unique nucleic acid sequence is then presented to a plurality of different collector binding sites where at least one of the sites comprises at least one collector molecule complimentary to the unique nucleic acid sequence. Unique nucleic acid sequences in the sample selectively hybridize to the bound complementary collector molecule and their presence is detected.

16 Claims, 2 Drawing Sheets

METHOD AND APPARATUS FOR DETECTION OF MULTIPLE NUCLEIC ACID SEQUENCES AND MULTIPLE ANTIGENS

This is a continuation-in-part application of application Ser. No. 09/025,470, filed Feb. 18, 1998.

FIELD OF THE INVENTION

The present invention relates in general to methods, devices and compositions useful in the detection of biologically active materials and in particular to methods, devices and compositions useful in the detection of nucleic acids and antigens. Three different general fields are improved upon by the present invention.

BACKGROUND OF THE INVENTION

The first field improved upon by the present invention is the field of nucleic acid diagnostics. The field of nucleic acid diagnostics uses the tools of molecular biology to detect the presence of bacterial and viral infectious agents, genetic variation, and diseases such as cancer. One of the first steps in nucleic acid diagnostics is generally the amplification of one or more target nucleic acid sequences specific for the biological entity of interest in one or more samples. This amplification step provides the sensitivity to detect very small numbers of nucleic acid molecules containing the target sequence(s). Several nucleic acid amplification methods have been developed, including the well-known polymerase chain reaction (PCR) as well as the ligase chain reaction (LCR) and the self-sustained sequence replication (3SR) method. The specificity of these amplification methods relies on the use of oligonucleotide primer sets which uniquely identify a particular target nucleic acid sequence. This specificity can be very high; for example, in multiplex PCR, different primer sets are used to amplify separate target sequences within the same nucleic acid molecule in a single tube.

Following the amplification step, the presence of a particular amplified target nucleic acid sequence is then determined by a variety of ways. One of the most common methods is direct visualization of the desired product by electrophoresing an aliquot of the amplification reaction in an agarose or acrylamide gel. Since the amplification products are separated on the basis of size, this detection method is precluded if discrimination between different amplification products, i.e., different target sequences, of about the same size is desired.

More sensitive detection methods involve hybridization of the amplified products with an oligonucleotide (oligo) probe having a sequence complementary to a portion of the target sequence of interest followed by detection of the oligo-target hybrid. These hybridization methods generally include immobilization of the amplified products or immobilization of the oligonucleotide probe to a solid support, wherein either the oligo or the target nucleic acid bears a detectable label. For example, T. R. Gingeras et al., "A Transcription-Based Amplification System" in PCR Protocols: A Guide to Method and Applications (Michael A. Innis et al. eds., 1990), pp. 245–252, herein incorporated by reference, disclose a bead-based sandwich hybridization method in which sephacryl beads containing an immobilized oligonucleotide specific for a segment of the target sequence were used to capture amplified products that had hybridized in solution to a $^{32}$P-labeled detection oligonucleotide specific for a different segment of the target sequence. The presence of the target sequence was detected by assaying the beads for radioactivity.

Other solid supports may be used to immobilize one of the hybridization partners. For example, in the well-known dot-blot method, aliquots of the amplified sample are dotted on a nylon membrane which is then probed with a labeled oligonucleotide. If detection of multiple target nucleic acid sequences is desired, this dot blot method can be quite time consuming in that for n target sequences, the membrane must be stripped between sequential hybridization with each of n probes, or alternatively, each amplified sample must be immobilized on n membranes and each membrane hybridized to one of n probes. This problem is addressed by the "reverse-dot blot" method disclosed by H. A. Erlich and T. L. Bugawan, "HLA DNA Typing" in PCR Protocols: A Guide to Method and Applications (Michael A. Innis et al. eds., 1990), pp. 261–271, herein incorporated by reference, in which the amplified product, labeled during amplification, is hybridized to an immobilized array of oligonucleotide probes.

Recently developed hybridization-based nucleic acid detection methods do not rely on amplification of a target sequence for sensitivity, but instead amplify the signal from each immobilized oligo-target hybrid. Such signal amplification methods include the branched DNA (bDNA) probe technology developed by Chiron (Emeryville, Calif.).

While the above-described reverse dot blot method allows for the simultaneous detection of multiple nucleic acid sequences, this method is not readily adaptable to economical large scale use or automation. For example, the production of multiple units, i.e., membranes containing duplicate arrays of oligonucleotide probes, requires precision spotting of equivalent amounts of probes to defined areas of replicate membranes in a sequential fashion. Moreover, performing detection of a large number of sequences with the reverse dot blot method requires covering a fairly large membrane surface area with hybridization reagents, some of which are expensive.

However, in many situations it would be advantageous to rapidly screen a sample for the presence of multiple nucleic acids simultaneously using a method that is economical to perform and amenable to automation. For example, in the biomedical field, it would be beneficial to have a technique to rapidly and economically screen donated blood from multiple individuals for different known pathogenic viruses. Also, due to the increasing concern about the potential use of biological weapons by terrorists and by armies in war, the ability to rapidly screen multiple air and water samples in the field for nucleic acids of known and/or unknown sequence could improve the ability to treat both civilian populations and military personnel exposed to such weapons. Finally, an optimal method for simultaneous detection of multiple nucleic acids would be capable of directly detecting small numbers of target nucleic acid sequences by increasing the hybridization signal. Such detection would lend the capability of detecting in a sample the presence of single pathogenic microorganisms which carry low copy numbers of the target nucleic acid sequence.

The second field improved by the present invention is the field of immunodiagnostics. Enzyme linked immunoassay, commonly referred to as ELISA, is a well known technique for the detection and measurement of antigens or antibodies in solution which uses enzyme-linked antigens or antibodies to detect an antigen-antibody reaction. This technique has been used in a variety of immunodiagnostic applications such as seriodiagnostics to detect antigens from a wide range of specific viruses, bacteria, fungi, and parasites, and to measure the presence of antibodies against these various microorganisms. ELISA is also used to monitor factors involved in noninfectious diseases such as hormone levels, hematological factors, serum tumor markers, drug levels, and antibodies.

Typically, the enzyme used in ELISA is selected from alkaline phosphatase, horseradish peroxidase, and beta-galactosidase and it is coupled to an antibody or antigen. The binding of the enzyme-linked antibody or antigen to its corresponding antigen or antibody is detected by adding substrates that, upon reaction with the enzyme, are converted into colored reaction products or give off luminescence.

An antigen-antibody reaction is traditionally defined as the interaction between an antigenic determinant, or epitope, on the antigen molecule and a corresponding antigen-combining site, or paratope, on the variable region of the antibody molecule. In addition to this interaction, the paratope on the antibody molecule may also serve as an antigenic site, i.e., be recognized by a paratope on the variable region of a second antibody molecule. In this situation, the paratope on the first antibody is referred to as the idiotope. Thus, in its broadest sense, the ELISA technique may be understood as capable of detecting the interaction of specific binding partners, or ligands, which include epitope-paratope interactions and idiotope-paratope interactions.

The type of binding partner interactions, which can be detected by ELISA, is partially illustrated by a recent description of a modified ELISA technique used to detect the presence of anti-HIV antibody in solution. Brennan et al., in *Protein Engineering* 7(4): 509–514 (1994), describes a modified alkaline phosphatase containing an epitope from the HIV-1 gp120 protein inserted onto its surface in the vicinity of the enzyme's active site. The activity of this modified alkaline phosphatase, which is comparable to the activity of wild type alkaline phosphatase, was reduced by almost half by the binding of an anti-gp120 monoclonal antibody to the gp120 epitope on the modified alkaline phosphatase.

One of the limitations of conventional ELISA methods is that they detect, in a linear or sequential fashion, only one type of antigen or antibody at a time. However, in many situations it would be advantageous to rapidly screen a sample for the presence of multiple antigens or antibodies simultaneously. For example, in the biomedical field, it would be beneficial to have a technique to rapidly determine which pathogen(s) of a number of possibilities has infected a patient so that an appropriate treatment can be implemented without the delay of additional screening. In addition, with the increasing concern about the potential use of biological and chemical weapons by terrorists against civilian populations and by armies in war as weapons of mass destruction, the ability to rapidly detect and identify multiple biological, chemical or toxin agents in the field could improve the ability to treat both civilian populations and military personnel exposed to such agents.

The third field improved by the present invention is the field of automated workstations. Such workstations are designed to automatically carry out sequential chemical reactions such as the amplification of DNA using the polymerase chain reaction.

State of the art automated workstations used in carrying out the polymerase chain reaction, such as Perkin-Elmer's ABI PRISM 877 integrated thermal cycler, automatically handle the cycling protocol. This cycling protocol consists of a standard multi-well thermal cycler integrated with a high-precision robot which conducts the pipetting of PCR primers, DNA polymerase, buffer, and other PCR reagents into individual tubes placed in the wells of the thermal cycler and the subsequent removal of the reaction tubes. The benefits of such an automated system is that the system frees researchers and lab assistants from manually pipetting the reagents into the individual reaction tubes and speeds the processing of samples by the use of multiple reaction tubes. In addition, such automated integrated thermal cycler systems reduce the chance for contamination from ubiquitous oligonucleotides which are found on almost every surface. Nonetheless, automated workstations work in a relatively slow step-wise fashion related in a large part to the physical constraints placed upon the robotic arm, which controls the automatic pipetting of aliquot and the subsequent removal and replacement of the reaction tubes. In addition, the movement of the robotic arm and the pipetting of PCR reagents into the reaction tubes still permits contamination of the reaction mixture by foreign oligonucleotides that might come in contact with the pipette orifice or be introduced by airborne particles. It would be very advantageous in the field of automated PCR workstations to have an apparatus which is capable of simultaneous amplification of oligonucleotides found in multiple samples and which eliminates the chance of contamination of the samples with stray oligonucleotides.

No related method, composition, or apparatus is known that uses a unique reporter molecule to identify the presence of the target antigen or target nucleic acid so as to permit the simultaneous detection of multiple nucleic acid sequences and/or multiple antigens from a biological sample and, wherein the sample containing the reporter molecule is continuously and automatically amplified in a closed apparatus before the ultimate detection of the presence of the reporter molecule is accomplished using electrochemiluminescent technology. Electrochemiluminescent technology is available from IGEN, Inc. of Gaithersburg, Maryland and is disclosed in detail in U.S. Pat. Nos. 5,310,687; 5,221,605; 5,238,808 and 5,147,806 which are herein incorporated by reference.

SUMMARY OF THE INVENTION

Accordingly, an object of the invention is to provide a method, such as an improved immunosorbent assay, for simultaneously detecting the presence of multiple target nucleic acids and/or multiple target antigens in a sample.

A further object of the present invention is to provide a novel composition of molecules useful for simultaneously detecting the presence of multiple target nucleic acids and/or multiple target antigens in a sample.

A further object of the present invention is to provide a unique thermal cycler useful in methodologies such as PCR which require the continuous heating and cooling of reagents and sample aliquots in an environmentally isolated manner.

An additional object of the present invention is to provide an extremely sensitive detection device for the rapid, simultaneous amplification and detection of multiple target nucleic acids and/or multiple target antigens in a sample.

These and other objects are achieved by construction of the following novel invention:

For detection of a target nucleic acid, one or more copies of a first oligonucleotide, which is complementary to a unique sequence of the target nucleic acid, are covalently attached to a support. Partially hybridized to the covalently bound first oligonucleotide(s) is a second oligonucleotide. The second oligonucleotide is itself partially complementary to the first oligonucleotide. Attached covalently to the partially complementary second oligonucleotide is an oligonucleotide reporter sequence comprising two primer sequences which flank an oligonucleotide sequence, which sequence uniquely identifies the target nucleic acid. Together the partially complementary second oligonucleotide and the unique oligonucleotide sequence flanked by primers comprise a unique reporter molecule.

For detection of a target antigen such as a hormone, antibody, nerve agent, drug, toxin, chemical compound, or protein, one or more molecules of a target antigen are covalently attached to a support so that at least one epitope is accessible. Bound to the epitope(s) of the covalently bound antigen(s) is a complementary antibody. Attached to the hybridized antibody is an oligonucleotide again comprising two primer sequences which flank an oligonucleotide sequence, which sequence uniquely identifies the target antigen. Together the complementary antibody and the unique oligonucleotide sequence flanked by primers comprise a unique reporter molecule.

If a target nucleic acid molecule is present in a sample, the unique nucleic acid sequence of the target nucleic acid molecule competitively binds with the complementary oligonucleotide covalently bound to the support. This displaces the previously hybridized unique reporter molecule into the sample.

Likewise, if a target antigen, such as a hormone, antibody, nerve agent, drug, toxin, chemical compound or protein, is present in a sample, the target antigen competitively binds with the complementary antibody. This releases the unique reporter molecule into the sample.

The sample, along with any displaced unique reporter molecule, is then washed from the support. Displaced unique reporter molecule(s) which comprise the two primer sequences and the sequence unique to the target nucleic acid molecule or antigen which the primers flank, are subsequently amplified and labeled using the Polymerase Chain Reaction (PCR) method. An improvement over the present PCR methodology lies in the automation of the amplification process, in addition to the protection of the sample from foreign oligonucleotide sequences. Such automation and protection is achieved by repeatedly passing the sample containing the unique reporter molecule, mixed with Ruthenium or Osmium labeled primers, and PCR reagents, through a conduit over a surface having dissimilar temperature zones. The continuous passage of the sample through the conduit across temperature gradients multiple times can yield the desired number of heating and cooling cycles thereby resulting in the amplification and labeling of the two primer sequences, along with the sequence that uniquely identifies the target nucleic acid or antigen.

After amplification of the two primer sequences along with the sequence unique to the target nucleic acid and/or antigen, a substrate or a chemical such as tripropylamine (TPA), an electrochemiluminescent reagent, is mixed into the sample before the sample is finally pumped through a collector cell containing a plurality of pre-positioned beads. Each of these pre-positioned beads has covalently attached to the bead a multiplicity of one particular oligonucleotide sequence complementary to each unique oligonucleotide sequence used to identify a specific target nucleic acid or antigen. The position of each bead is known in relation to the particular complementary unique oligonucleotide sequence bound to the bead. Thus, in this example, when a Ruthenium or Osmium labeled oligonucleotide comprising the two primer sequences and the sequence unique to the target nucleic acid molecule and/or antigen is present in the sample, the labeled unique portions of the amplified oligonucleotide hybridizes to one of the pre-positioned beads that contains a complementary bound oligonucleotide sequence. The pre-positioned beads are then subjected to a small electrical current which causes any labeled oligonucleotides bound to a specific bead to emit light that is measured by a luminometer, such as a photomultiplier tube, with the output of the luminometer available for analysis.

DETAILED DESCRIPTION OF THE INVENTION

As indicated above, the present invention provides rapid, simultaneous detection of minute quantities of multiple nucleic acids and/or antigens in a sample. Nucleic acids or antigens detectable by the invention are referred to as target molecules and include nucleic acids found in and antigens derived from microorganisms and other pathogens, toxin molecules and other chemical agents such as drugs and nerve agents, and antibodies specific for the foregoing materials. Target molecules may also be self-antibodies generated in autoimmune diseases. A target molecule is detected by the target molecule's displacement of a reporter molecule from the reporter molecule's support. The displaced reporter molecule is subsequently amplified using the patented PCR process and labeled utilizing oligonucleotides which can be labeled with Ruthenium or Osmium. Exceedingly low copy numbers of a target nucleic acid or antigen can therefore be subsequently detected by the amplification and labeling of the primer flanked oligonucleotide sequence which is then captured for analysis.

Figure 1:
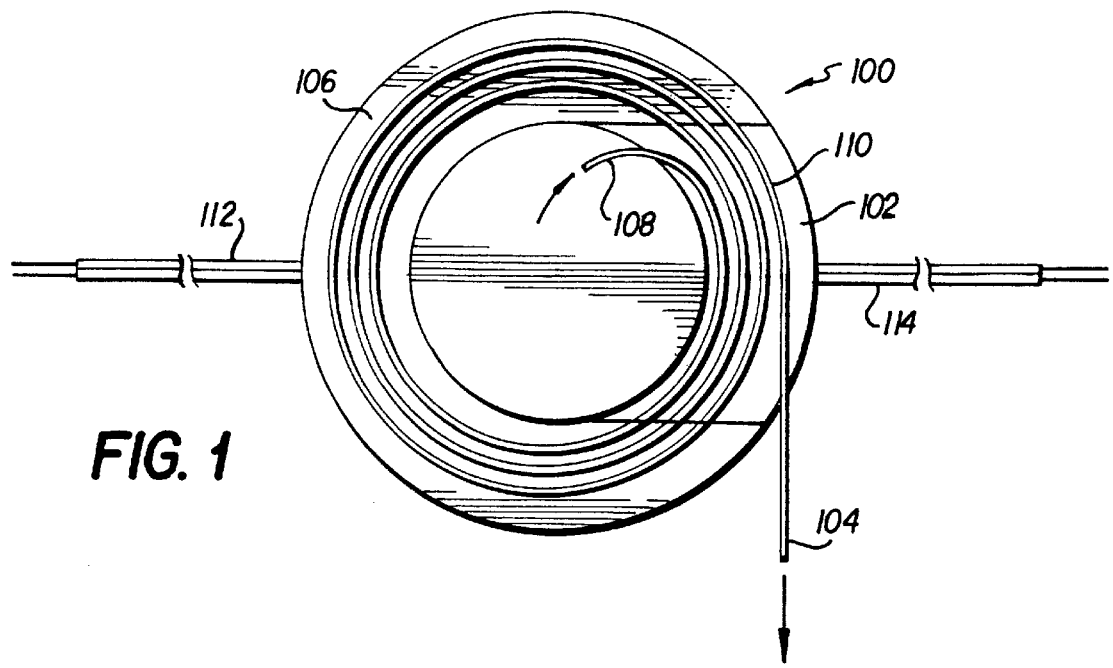
FIG. 1 is a schematic representation of a thermal cycler embodiment of the present invention.

FIG. 1 is a schematic representation of the thermal cycler 100 in the preferred embodiment of the invention, showing the arrangement of a micro-capillary tube 110 over and in intimate contact with a surface 102 having at least one heated denaturing sector 106 and at least one annealing/extension cooling sector 102, which sector surfaces thereby cause the rapid and continuous heating and cooling of reagents and sample aliquots that are transported through the micro-capillary tube through inlet 108, through the micro-capillary tube 110 and discharged through the outlet 104. Although a micro-capillary tube 110 is shown, any suitable conduit for passage of reagents and sample aliquots, such as a channel or a trough, is encompassed by the present invention. In this example, the energy source for the heated sector(s) is supplied by electrical energy supplied by electrical leads 112. In similar fashion, sector(s) can be heated or cooled by an appropriate thermoelectric device supplied by electrical current by electrical leads 114. The heating and cooling of these sectors can also be accomplished by the use of a suitable material pumped into the interior of the sectors or by any other construction that allows a temperature differential. Such suitable materials include liquid substances and gases. As is apparent, the surface 102 of the thermal cycler 100 can be conical, cylindrical, spherical or any number of other geometric shapes. Likewise the configuration of the micro-capillary tube 110 across the surface of the thermal cycler 100 can likewise take many alternate configurations from the spiral shape as shown, including such configurations as repeating loops or square patterns.

Figure 2:
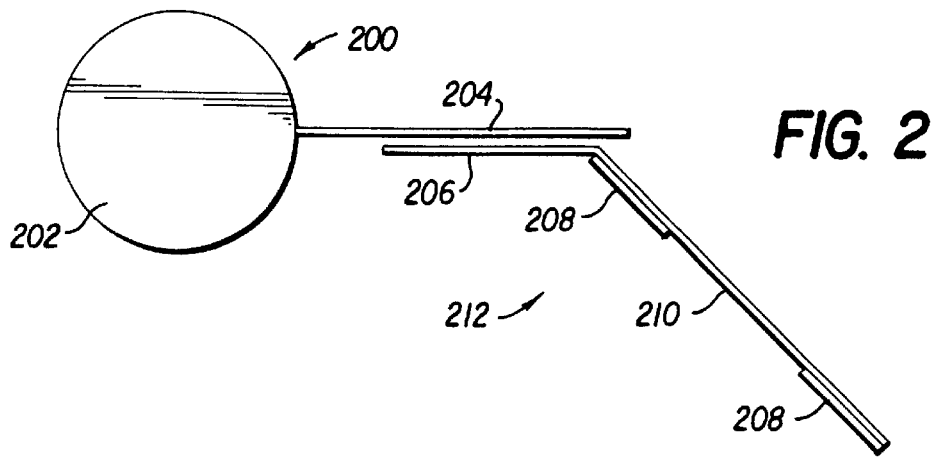
FIG. 2 is a schematic representation of a first reporter column support bead.

FIG. 2 is a schematic representation of a reporter column support bead 200, showing a reporter molecule 212 partially hybridized to an oligonucleotide 204 complementary to the target nucleic acid. The complementary oligonucleotide 204 is covalently bound to a support bead 202. This arrangement permits a target nucleic acid in a sample to competitively hybridize with the support bead bound oligonucleotide 204 and to thereby displace the reporter molecule 212 into solution. Also shown in FIG. 2 are the various elements of the reporter molecule 212. These elements include an oligonucleotide 206, partially complementary to oligonucleotide 204, attached covalently to a uniquely identifying oligonucleotide 210 which is itself flanked by two PCR primer sites 208.

Figure 3:
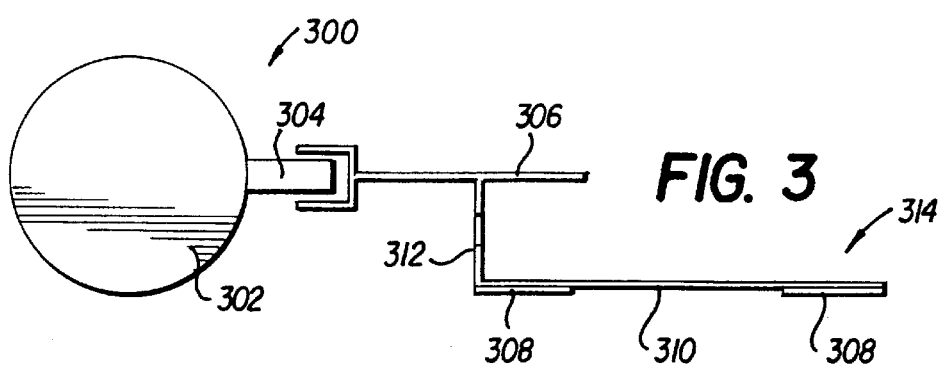
FIG. 3 is a schematic representation of a second reporter column support bead.

FIG. 3 is a schematic representation of another reporter column support bead 300, according to the invention, showing a reporter molecule 314 comprising a uniquely identifying oligonucleotide sequence 310 flanked by two PCR primer binding sites 308, which reporter molecule 314, i.e. oligonucleotide 310 and PCR primer binding sites 308, is covalently bound through a linker molecule 312 to an antibody molecule 306 that has high specificity, but low to moderate affinity, for the target antigen 304. The antibody molecule 306 is itself hybridized to a target antigen molecule 304, which is itself covalently bound to a reporter column support bead 302. This arrangement likewise permits a target antigen in a sample to competitively displace the antibody molecule 306 and the associated, unique reporter molecule 314 into solution. The linker molecule can be a streptavidin-biotin linkage as described in U.S. Pat. No. 5,635,602 titled "Design and Synthesis Bispecific DNA-Antibody Conjugates", which is incorporated herein by reference, or one of a number of other linker molecules known to those in the art field which are useful for this purpose.

Figure 4:
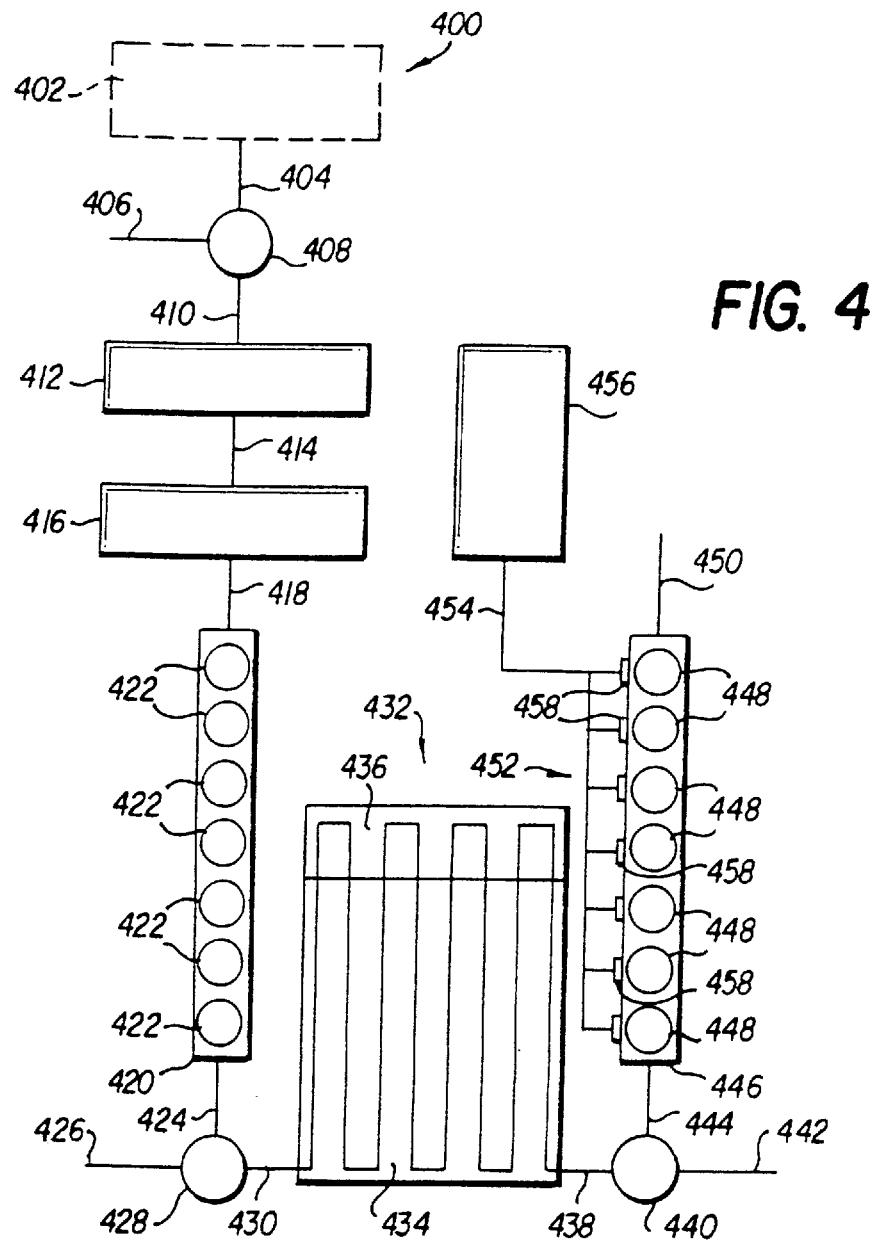
FIG. 4 is schematic representation of a detection system according to the present invention.

FIG. 4 is a schematic representation of a detection system 400 according to the invention, showing a collector 402 through which atmospheric, liquid or solid samples are collected for detection. The collector 402 is connected by conduit 404 with a device 408 for mixing the sample with appropriate buffers and reagents inserted through inlet 406 to lyse the membranes of cells in the sample and so inactivate or treat the sample. In this example, the sample is then passed through conduit 410 into heater 412 in order to further inactivate any biologically active substances and to denature nucleic acids in the sample. In this example, the sample is then fed from the heater 412 through conduit 414 into a filter device 416 where unwanted particulates are caught and removed. The filtering of the sample is an option which may or may not be bypassed according to the type of sampling one intends to conduct. Obviously liquid samples do not require a filtering step if the heating step does not result in the precipitation of the components in the sample. After passing through the filter device 416, the sample is fed through conduit 418 into the reporter column 420 containing at least one reporter molecule bound support bead(s) 422 over which the sample flows. The sample then leaves the reporter column 420 by way of conduit 424 to a mixing and/or pumping device 428 into which PCR reagents and labeled primers, in this example Ruthenium or Osmium labeled primers, are introduced into the sample through inlet 426. The sample and PCR reagents exit the mixing and pumping device 428 through micro-capillary tube 430, which tube then passes in a repetitive fashion over temperature gradients 434 and 436 of a thermal cycler 432. The sample flows through the micro-capillary tube to the outlet 438 where the sample enters another mixing device 440 where an assay buffer is introduced through inlet 442 and mixed with the sample.

The sample then exits the mixing device 440 and flows through conduit 444 into the collector/assay column 446. The collector/assay column 446 contains pre-positioned support beads 448 containing capture oligonucleotides for each unique reporter molecule employed in the reporter column support beads 422. The sample finally exits the collection/assay column 446 through outlet 450 after having passed over the collector/assay support bead(s) 448.

Figure 5:
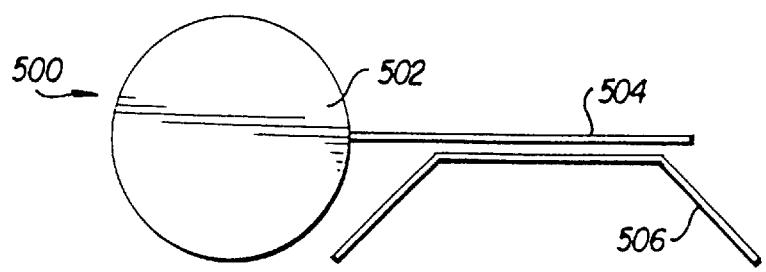
FIG. 5 shows an enlarged schematic representation of a collector/assay column support bead of the system of FIG. 4.

FIG. 5 shows an enlarged schematic representation of one of these collector column support beads 502 showing the bead bound covalently to an oligonucleotide 504 which is complementary to the amplified and labeled uniquely identifying oligonucleotide 506. The enlarged schematic representation 500 shows the amplified, labeled and primer flanked uniquely identifying oligonucleotide 506 hybridized with the complementary support bound oligonucleotide 504.

In this example, FIG. 4 further shows a schematic representation of the device 452 used for the electrical excitation of a labeled oligonucleotide 506 and for the detection of light emitted from these same labeled oligonucleotides 506 which oligonucleotides have been captured and hybridized with the complementary support bound oligonucleotide 504. The emitted light is indicative of the presence of a target nucleic acid or antigen. The excitation/detection device 452 is preferably connected through lead 454 to a device 456, typically a microprocessor, with the capability to record and display such positive light signals and correlating such signals with the presence of a particular target nucleic acid or antigen. In use, the light is read by a luminometer, typically a photomultiplier tube, 458 connected by lead 454 to the device 456. In this example, each luminometer 458 is placed in close physical proximity to each of the collector/assay support beads 448. Alternatively, a light pipe can be used to transmit the light to the luminometer.

The present invention also includes modifying the above-described embodiments of reporter column support bead 200 and 300 by the switching of molecules 204 and 206 as shown in FIG. 2 and the switching of the molecules labeled 304 and 306 as shown in FIG. 3. The effect of switching molecules 204 and 206 would be that any target nucleic acid in the sample would competitively bind with its complementary reporter molecule 212 and would then travel in solution bound with the rest of the reporter molecule 212. Molecule 206, the oligonucleotide partially complementary to the oligonucleotide identified as molecule 204 would remain attached to the support bead 202 and would be available for subsequent hybridization with a fresh reporter molecule 212 of this alternate version of molecule 200. The reporter column beads could therefore be recharged in anticipation of a future exposure to the target nucleic acid.

Another embodiment of reporter column support bead 200 is arrived at by eliminating oligonucleotide 206 and substituting in its place the uniquely identifying oligonucleotide 210 which is itself flanked by two PCR primer sectors 208. In such an arrangement the uniquely identifying oligonucleotide 210 is partially complimentary and is bound to molecule 204.

Similarly, the epitope exposing target antigen and complementary antibody identified as elements 304 and 306 respectively in FIG. 3 can be switched. The effect of such a switch would be that the target antigen 304 would competitively bind to the support bead-bound antibody 306 and so displace in the sample the antigen 304, which would then be bound to the primer flanked unique oligonucleotide molecule 314 through linker molecule 312. To recharge the support bound antibody molecule 306 it would be first necessary to melt bound antigen off of the support bound antibody 306 by the use of elevated temperatures. Alternative measures exist for recharging the support bond antibody molecule 306. Such means include the use of passing a heated, high pH, detergent containing, buffer solution over the reporter column support beads 422. In any case the column 420 would then be washed, new reporter molecules 210 or 314 washed through the column 420 and the column 420 thereafter washed and tested.

Procedures for predicting and determining antigenic sites on target antigens or antibodies are well-known in the art. For example, antigenic sites to proteins of pathogens of interest may be selected using a hydrophobicity computer analysis, e.g., Hopp, T. P. and Woods, K. R., *Proc. Natl. Acad. Sci., USA*, 78, 3824–8 (1981), herein incorporated by reference. Candidate antigenic sites are screened experimentally to select those which generate antibodies that also recognize the pathogenic protein of interest and have optimal binding characteristics and minimal cross reactivity. This screening is considered routine experimentation by those skilled in the art.

Recently developed electrochemiluminescence (ECL) technology (available from IGEN, Gaithersburg, Md.), as used in the present invention, enables the present invention to report the presence of even exceedingly low copy numbers of amplified primer flanked oligonucleotide reporter sequences, by labeling the primer molecules with molecules, such as Ruthenium or Osmium. The hybridization of labeled oligonucleotide with its complementary support bound oligonucleotide will be referred to as a bound binding site. Applying a low voltage through device 452 to an electrode positioned near the bound binding site oxidizes the label and its substrate, tripropylamine (TPA), to form strong oxidant and reduction compounds, respectively, which then react to form an excited state of the label that subsequently decays to its starting ground state while releasing a photon at 620 nm. (See, e.g., Michael Carlowicz, "Electrochemiluminescence Could Spark an Assay Revolution", Clin. Lab. News, Vol. 21, p. 1–2 (Aug. 1995), herein incorporated by reference.) The photon emissions are detected using a luminometer identified in FIG. 4 as element 458.

The antigen-primer flanked oligonucleotide and the oligonucleotide-primer flanked oligonucleotide complexes may be generated by chemically coupling the individual molecules using coupling reagents or during synthesis. Coupling reagents include, but are not limited to, sulfo-SMCC (Calbiochem, San Diego, Calif., Prod No.: 573115). Additionally, for the oligonucleotide-primer flanked oligonucleotide complexes, the complex may a single polypeptide obtainable from commercial houses specializing in the synthetic manufacture of oligonucleotides. Ruthenium-labeled molecules may be prepared using ORIGEN® TAG-NHS ester (IGEN, Inc.), which is a salt of ruthenium (II) tris(bipyridyl) chelate, a water soluble compound that is chemically modified on one of the bipyridyl ligands to enable labeling of proteins, haptens, and nucleic acids.

Attachment of molecules to a solid support to form a binding site is well known in the art. The attachment may be either noncovalent, e.g., the complex binds to the solid support through adsorption, or covalent, e.g., the complex is chemically coupled to the solid support via a linker molecule. Preferably the attachment is covalent so that the binding sites can be recharged with fresh reporter molecules without the loss of the potentially expensive or toxic oligonucleotide or antigen which had been previously bound to the solid support. The support is selected from substrates such as glass or plastic beads, membranes, microplates, magnetic particles, latex particles, nitrocellulose particles, and glass or plastic strips or any other materials to effectively immobilize said ligands. The binding site may comprise only one molecule of the complex. Preferably the binding site contains a plurality of molecules of the complex. Preferred embodiments of the reporter column support beads are illustrated in FIGS. 2 and 3.

The term antibody is intended to include: monoclonal antibodies generated using cells obtained from mice immunized with the target antigen, the target antigen conjugated to a carrier molecule, or portions of the target antigen; monoclonal antibodies obtained by screening microorganisms genetically engineered to express the H- and L-chain repertoires of a particular species; monoclonal antibodies expressed by recombinant phage in which the expressed mAbs have been engineered to have desirable characteristics such as improved relative affinities for the target antigen; fragments of the aforesaid monoclonal antibodies, e.g., $(Fab)_2$ fragments; and monovalent antibodies. To construct a binding site of the preferred embodiment, a solid support containing the immobilized antigen is treated to prevent nonspecific adsorption of antibody using methods known in the art and then the mAb is allowed to bind to the target antigen.

After the reporter binding site is constructed, its binding activity is assayed to determine if it is suitable for detecting the presence of the corresponding target antigen in a solution. A reporter binding site has a suitable binding activity if the antibody of the immobilized antigen-antibody complex can specifically capture the target antigen molecule from the solution presented to the reporter binding site.

Once collector binding sites for different target reporter molecules are constructed, one or more binding sites for different target molecules are arranged in a known relationship to allow simultaneous detection of multiple nucleic acids and/or antigens in a sample. The nature of this arrangement is such that the sample may be presented to the binding sites in a single operation to provide essentially simultaneous contact of the sample with the different collector binding sites. Furthermore, the arrangement must allow the different binding sites to be distinguishable from each other.

For example, the collector binding sites may be arranged on the surface of a membrane and the sample applied to the membrane or strip by the single operation of spraying the membrane with the sample or dipping the membrane into the sample. Preferably, the binding site comprises a unique oligonucleotide sequence attached to a bead and the different binding sites, i.e., different beads, are arranged along the length of a collector tube as shown in FIG. 4. In this embodiment, simultaneous contact of the sample with the binding sites is achieved by the single operation of flowing the sample from one end of the tube to the other end. For example, the tube may be held in a vertical or horizontal position and the sample presented to the binding sites by the single operation of applying the sample to one end of the column such that it moves across the column or by the single operation of applying suction to one end of the column to draw the sample into the column from its other end. In another embodiment of this invention, the collector/assay column support beads 448 may have a wafer-like shape which permits a larger surface area to be presented to the luminometer 458.

The invention also provides a detection device for rapidly testing a sample for the presence of multiple antigens or antibodies comprising at one or more of the above described collector binding sites arranged in a known order with respect to each other. The shape, size and relative positions of the binding sites are a matter of design choice and will depend somewhat upon the support chosen to immobilize the ligand-enzyme complexes.

In a preferred embodiment, the different reporter binding site(s) of the detection device comprise bead(s) to which different oligonucleotides are attached and the different reporter binding site(s) are placed in a known order in a tube. Preferably, the different reporter binding site(s) are separated from each other by empty bead(s), i.e., lacking oligonucleotides. Thus, if a plurality of beads is used in each reporter binding site, the different reporter binding sites will have the shape of bands along the tube. The tube may be transparent to allow detection of light emission with one or more luminometers disposed outside the tube. For example, a single luminometer may be moved the length of the tube stopping at the location of each reporter binding site to monitor for light emission from that site, or multiple luminometer detectors may be positioned next to the location of each binding site as shown in FIG. 4. Light guides can also transport light emitted to one or more remotely located luminometers. Alternatively, the tube is nontransparent and is provided with a means for detecting light emission from the banded reporter binding sites, e.g., by a plurality of miniature luminometers attached to the interior wall of the tube at positions corresponding to the location of each reporter binding site. As is evident, the detection methodology can be based upon other detection techniques as well, such as plasma resonance, pH changes, interference patterns or color changes.

Each luminometer 458 is operably connected through lead 454 to a microprocessor 456 which has an analyzer for analyzing the light signals detected by the luminometers 458 and a reporter for reporting whether specific nucleic acids or antigens were detected in the sample. This report may be visual, i.e., such as lights that turn on when one or more specific target nucleic acids or antigens are detected, or a printout which lists the nucleic acids or antigens detected. Alternatively, or in addition to a visual report, the report may include an audible alarm which is activated when one or more target nucleic acids and/or one or more target antigens are detected. The system also comprises a continuous flow mixer 408 which has means for mixing the sample and substrate and also means for pumping the sample through the reporter column, thermal cycler and collector/assay column.

The principles, preferred embodiments and modes of operation of the present invention have been described in the foregoing specification. The invention, which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A method for detecting the presence of extremely low levels of multiple target nucleic acid sequences and/or multiple target antigens in a sample, comprising:

(a) presenting a sample suspected of containing targets selected from the group consisting of nucleic acids, antigens, and mixtures of at least one nucleic acid and at least one antigen, to a plurality of collector molecules comprised of a first complementary molecule and a second complementary molecule, the first and second complementary molecules being hybridized and bound to one another, the first complementary molecule being attached to a support medium and the second complimentary molecule comprises a complimentary binding portion and a unique reporter oligonucleotide molecule flanked by primer binding sites such that the targets in the sample displace the second complementary molecule which is bound to the first complementary molecule and hybridize with the first complementary molecule thereby releasing the second complementary molecule into the sample;

(b) washing the sample containing the released second complementary molecule;

(c) mixing the sample containing the released second complementary molecule with labeled primers and polymerase chain reaction reagents;

(d) amplifying the unique reporter oligonucleotide molecule and flanking primer binding sites of the second complementary molecule by passing the sample through a conduit in intimate contact with a surface having a temperature gradient suitable for amplification or reaction conditions;

(e) presenting the sample containing amplified unique reporter nucleic acid molecules to a plurality of different binding sites arranged in a known order, with respect to each other, wherein a third molecule complementary to the amplified unique reporter molecule is bound to at least one of the collector binding sites; and (f) detecting at least one collector binding site for a light emission indicative of the presence of an amplified and labeled unique reporter molecule bound to the third complementary molecule.

2. The method of claim 1, further comprising, before the detecting step:

washing the different collector binding sites to remove unbound molecules from the collector binding sites.

3. The method of claim 1, further comprising, before the first presenting step; mixing a sample suspected of containing target nucleic acids or antigens with buffered detergent; and, filtering to remove unwanted particulates.

4. The method of claim 2, further comprising:

heating the sample to inactivate reactive substances and to denature nucleic acids between the mixing and filtering steps.

5. The method of claim 1, wherein the first complementary molecule comprises a oligonucleotide sequence complementary to a unique sequence of the target nucleic acid and the complementary binding portion of the second complementary molecule comprises a complementary oligonucleotide sequence.

6. The method of claim 1, wherein the first complementary molecule comprises a oligonucleotide sequence homologous to a unique sequence of the target nucleic acid and the complementary binding portion of the second complementary molecule comprises the oligonucleotide sequence partially complementary to the first complementary molecule.

7. The method of claim 1, wherein the first complementary molecule comprises the target antigen and the complementary binding portion of the second complementary molecule comprises a complementary antibody which has a high specificity and low to moderate binding affinity for the target antigen.

8. The method of claim 1, wherein the first complementary molecule comprises an antibody and the complementary binding portion of the second complementary molecule comprises the target antigen to which the antibody has a high specificity and low to moderate binding affinity.

9. An apparatus, comprising:

(a) a reporter column having at least one sample inlet and outlet, (b) a support medium, wherein said support medium is enclosed and exposably arranged within the reporter column;

(c) a collector molecule comprising a first partially complementary and a second partially complementary molecule, said first and second partially complementary molecule being partially hybridized and bound to one another, said second partially complementary molecule comprising a complementary binding portion and a unique reporter oligonucleotide molecule flanked by primer binding sites, and said first complementary molecule fixedly attached to said support medium;

(d) a first mixer having at least one sample inlet, one sample outlet and one inlet for labeled primers and reagents, said sample inlet of the first mixer is conductively connected to the outlet of the reporter column;

(e) a second mixer having at least one sample inlet, one sample outlet and one assay buffer inlet;

(f) a collector column having at least one sample inlet and outlet, said sample inlet of the collector column is conductively connected to the sample outlet of the second mixer;

(g) a conduit in intimate contact with a surface having a temperature gradient suitable for amplification or reaction conditions, the inlet of said conduit is conductively connected to the outlet of the first mixer, and the outlet of said conduit is conductively connected to the inlet of the second mixer inlet;

(h) a plurality of different collector binding sites, arranged in a known order, with respect to each other wherein a third molecule complementary to the amplified unique reporter molecule is bound to at least one of the collector binding sites, said plurality of different collector binding sites are enclosed and exposably arrange within the collector column; and (i) an excitator/detector arrayed above the surface of the collector binding sites for electrically exciting at least one collector binding site and for detecting a light emission indicative of the presence of an amplified and labeled unique reporter molecule bound to the third complementary molecule.

10. The apparatus of claim 9, further comprising:

(a) a third mixer having at least one sample inlet, one sample outlet, and one buffer detergent inlet; and (b) a filter having at least one inlet and outlet, said third mixer outlet conductively connected to the filter inlet and the filter outlet is conductively connected to the inlet of the reporter column.

11. The apparatus of claim 9, further comprising:

(a) a third mixer having at least one sample inlet, one sample outlet and one buffer detergent inlet;

(b) a heater having at least one inlet and one outlet; and (c) a filter having at least one inlet and outlet, said sample outlet of the third mixer is conductively connected to the inlet of the beater, the outlet of the heater is conductively connected to the inlet of the filter and the outlet of the filter is conductively connected to the inlet of the reporter column.

12. The apparatus of claim 7 wherein the first complementary molecule comprises an oligonucleotide sequence complementary to a unique sequence of the target nucleic acid and the complementary binding portion of the second complementary molecule comprises a partially complementary oligonucleotide sequence.

13. The apparatus of claim 9, wherein the first complementary molecule comprises an oligonucleotide sequence homologous to a unique sequence of the target nucleic acid and the complementary binding portion of the second complementary molecule comprises the oligonucleotide sequence partially complementary to the first complementary molecule.

14. The apparatus of claim 9, wherein the first complementary molecule comprises the target antigen and the complementary binding portion of the second complementary molecule comprises a complementary antibody which has a high specificity and low to moderate binding affinity for the target antigen.

15. The apparatus of claim 9, wherein the first complementary molecule comprises an antibody and the complementary binding portion of the second complementary molecule comprises the target antigen to which the antibody has a high specificity and low to moderate binding affinity.

16. A thermal cycler, comprising;

(a) a surface having differentially heated sectors; and (b) a conduit in intimate contact with the differentially heated sectors such that a sample containing reagents is alternatively heated and cooled by the differentially heated sectors as it passes through the conduit sufficiently to perform a desired process or chemical reaction, wherein the conduit has varying internal dimensions which slows or speeds up the flow of the sample to be heated or cooled.

* * * * *